US006806258B2

(12) United States Patent
Monia

(10) Patent No.: US 6,806,258 B2
(45) Date of Patent: Oct. 19, 2004

(54) ANTISENSE OLIGONUCLEOTIDE MODULATION OF RAF GENE EXPRESSION

(75) Inventor: Brett P. Monia, LaCosta, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/057,550

(22) Filed: Jan. 25, 2002

(65) Prior Publication Data

US 2003/0032607 A1 Feb. 13, 2003

Related U.S. Application Data

(63) Continuation of application No. 09/506,073, filed on Feb. 18, 2000, which is a continuation-in-part of application No. 09/143,214, filed on Aug. 28, 1998, now Pat. No. 6,090,626, which is a continuation of application No. 08/756,806, filed on Nov. 26, 1996, now Pat. No. 5,952,229, which is a continuation of application No. PCT/US95/07111, filed on May 31, 1995, and a continuation of application No. 08/250,856, filed on May 31, 1994, now Pat. No. 5,563,255, which is a continuation-in-part of application No. 08/888,982, filed on Jul. 7, 1997, now Pat. No. 5,981,731, and a continuation-in-part of application No. PCT/US98/13961, filed on Jul. 6, 1998.

(51) Int. Cl.[7] .......................... C07H 21/00; C12Q 1/68

(52) U.S. Cl. ............................ 514/44; 435/6; 435/325; 435/375; 536/23.1; 536/24.5

(58) Field of Search ................................ 514/44; 435/6, 435/325, 375; 536/23.1, 24.3, 24.32, 24.5

(56) References Cited

U.S. PATENT DOCUMENTS

| | | | | | |
|---|---|---|---|---|---|
| 4,806,463 | A | | 2/1989 | Goodchild et al. | 435/5 |
| 4,871,838 | A | | 10/1989 | Bos et al. | 536/27 |
| 5,004,810 | A | | 4/1991 | Draper et al. | 536/27 |
| 5,034,506 | A | | 7/1991 | Summerton et al. | 528/391 |
| 5,087,617 | A | | 2/1992 | Smith | 514/44 |
| 5,098,890 | A | | 3/1992 | Gewirtz et al. | 514/44 |
| 5,135,917 | A | | 8/1992 | Burch | 514/44 |
| 5,166,195 | A | | 11/1992 | Ecker et al. | 514/44 |
| 5,194,428 | A | | 3/1993 | Agrawal et al. | 514/44 |
| 5,264,423 | A | | 11/1993 | Cohen et al. | 514/44 |
| 5,276,019 | A | | 1/1994 | Cohen et al. | 514/44 |
| 5,286,717 | A | | 2/1994 | Cohen et al. | 514/44 |
| 5,563,255 | A | * | 10/1996 | Monia et al. | 536/24.31 |
| 5,952,229 | A | * | 9/1999 | Monia et al. | 435/375 |
| 5,985,558 | A | * | 11/1999 | Dean et al. | 435/6 |

FOREIGN PATENT DOCUMENTS

| | | | | |
|---|---|---|---|---|
| WO | WO 93/04170 | | 3/1993 | |
| WO | WO 93/06248 | | 4/1993 | |
| WO | WO 93/13121 | * | 7/1993 | C07H/21/04 |
| WO | WO 94/15645 | | 7/1994 | |

OTHER PUBLICATIONS

Agrawal et al., TIBTECH 1996. 14:376–380.*
Bonner et al., Nucleic Acids Res. 1986. 14 (2), 1009–1015.*
Tamm, I. et al. The Lancet. Aug. 2001. 358: 489–497.*
Gewirtz et al., Proc. Natl. Acad. Sci. v 93, pp. 3161–3163.*
Braasch, D. A. Biochemistry. Apr. 2002; 41(14): 4503–4510.*
Branch, A. D., (1998). Trends Biochem Sci. Feb. 1998;23(2):45–50.*
J. Biol. Chem. 1991 266(23) 14964–14969.*
J. Clin. Inv. 1993, 92: 194–202.*
Anfossi et al., "An oligomer complementary to c–myb–encoded mRNA inhibits proliferation of human myeloid leukemia cell lines", *Proc. Natl. Acad. Sci.* 1989, 86.
App et al., "Epidermal Growth Factor (EGF) Stimulates Association and Kinase Activity of Raf–1 with the EGF Receptor", *Mol. Cell Biol.* 1991, 11, 913–919.
Holt et al., "An Oligomer Complementary to c–myc mRNA Inhibits Proliferation of HL–60 Promyelocytic Cells and Induces Differentiation", *Mol. Cell Biol.* 1988, 8, 963–.
Kingston, R.E., in *Current Protocols in Molecular Biology*, John Wiley and Sons, NY.
P.E. Nielsen et al., "Sequence–Selective Recognition of DNA by Strand Displacement with a Thymine–Substituted Polyamide", *Science* 1991, 254, 1497.
Rapp et al., "The raf oncogenes", *The Oncogene Handbook*, E.P. Reddy, A.M. Skalka and T. Curran, eds., Elsevier Science Publishers, New York, 1988, pp. 213–253.
Riedel et al., "The Mitogenic response of T cells to interleukin–2 requires Raf–1", *Eur. J. Immunol.* 1993, 23, 3146–3150.
Sambrook et al., "Labeling the 5' Terminus of DNA with Bacteriophage T4 Polynucleotide Kinase", *Molecular Cloning. A Laboratory Manual*, Cold Spring Habor Laboratory Press, 1989, vol. 2, p. 10.59.
Sambrook et al., "Labeling of Synthetic Oligonucleotides by Phosphorylation with Bacteriophage T4 Polynucleotide Kinase", *Molecular Cloning. A Laboratory Manual*, Cold Spring Habor Laboratory Press, 1989, vol. 2, pp. 11.31–11.32.
Stanton and Cooper, "Activation of Human raf Transforming Genes by Deletion of Normal Amino–Terminal Coding Sequences", *Mol. Cell. Biol.* 1987, 7, 1171–1179.

(List continued on next page.)

*Primary Examiner*—Sean McGarry
*Assistant Examiner*—James D Schultz
(74) *Attorney, Agent, or Firm*—Licata & Tyrrell P.C.

(57) ABSTRACT

Oligonucleotides are provided which are targeted to nucleic acids encoding human raf and capable of inhibiting raf expression. The oligonucleotides may have chemical modifications at one or more positions and may be chimeric oligonucleotides. Methods of inhibiting the expression of human raf using oligonucleotides of the invention are also provided. The present invention further comprises methods of inhibiting hyperproliferation of cells and methods of treating or preventing conditions, including hyperproliferative conditions, associated with raf expression.

2 Claims, No Drawings

OTHER PUBLICATIONS

Tornkvist et al., “Inhibition of Raf–1 Kinase Expression Abolishes Insulin Stimulation of DNA Synthesis in H4IIE Hepatoma Cells”, *J. Biol. Chem.* 1994, 269, 13919–13921.
Wickstrom et al., Human promyelocytic leukemia HL–60 cell proliferation and c–myc protein expression are inhibited by an antisense pentadecadeoxynucleotide.
Maister, P., “Isis’ Antisense Drug Shows Promise for Retinitis”, *BioWorld Today*, Apr. 29, 1994, p.3.
Bennett et al., “Inhibition of Vascular Smooth Muscle Cell Proliferation. In Vitro and in Vivo by C–myc Antisense Oligodeoxynucleotides”, *J. Clin. Invest.* 1994, 93, 820–828.
*BioWorld Today*, Chiron, CytoMedUnite To develop Complement Inhibitors, Apr. 29, 1994, p 3.
Glen Research, Sterling VA. See 1993 Catalog of Products for DNA Research, Glen Research, Sterling VA, p. 21.
Isobe et al., “Early Detection of Rejection and Assessment of Cyclosporine Therapy by $^{111}$In Antimyosin Imaging in Mouse Heart Allografts”, *Circulation*1991, 84, 1246–1255.
Sambrook et al., *Molecular Cloning. A Laboratory Manual*, Cold Spring Habor Laboratory Press, 1989, vol. 2, p. 10.59.
Sambrook et al., *Molecular Cloning. A Laboratory Manual*, Cold Spring Habor Laboratory Press, 1989, vol. 2, pp. 11.31–11.32.
Rasouli–Nia et al., “High Raf–1 Kinase Activity Protects Human Tumor Cells against Paclitaxel–induced Cytotoxicity[1]”, *Clinical Cancer Research*, 1998 4; 1111–1116.

* cited by examiner

ANTISENSE OLIGONUCLEOTIDE MODULATION OF RAF GENE EXPRESSION

INTRODUCTION

This application is a continuation of Ser. No. 09/506,073 filed Feb. 18, 2000, which is a continuation-in-part of Ser. No. 09/143,214 filed Aug. 28, 1998 now issued as U.S. Pat. No. 6,090,626, which is a continuation of Ser. No. 08/756,806 filed Nov. 26, 1996 now issued as U.S. Pat. No. 5,952,229, which is a continuation of PCT/US95/07111 filed May 31, 1995 and Ser. No. 08/250,856 filed May 31, 1994 now issued as U.S. Pat. No. 5,563,255. This application is also a continuation-in-part of Ser. No. 08/888,982, filed Jul. 7, 1997 now issued as U.S. Pat. No. 5,981,731 and corresponding PCT application PCT/US98/13961 filed Jul. 6, 1998. Each of these applications is assigned to the assignee of the present invention.

FIELD OF THE INVENTION

This invention relates to compositions and methods for modulating expression of the raf gene, a naturally present cellular gene which has been implicated in abnormal cell proliferation and tumor formation. This invention is also directed to methods for inhibiting hyperproliferation of cells; these methods can be used diagnostically or therapeutically. Furthermore, this invention is directed to treatment of conditions associated with expression of the raf gene.

BACKGROUND OF THE INVENTION

Alterations in the cellular genes which directly or indirectly control cell growth and differentiation are considered to be the main cause of cancer. The raf gene family includes three highly conserved genes termed A-, B- and c-raf (also called raf-1). Raf genes encode protein kinases that are thought to play important regulatory roles in signal transduction processes that regulate cell proliferation. Expression of the c-raf protein is believed to play a role in abnormal cell proliferation since it has been reported that 60% of all lung carcinoma cell lines express unusually high levels of c-raf mRNA and protein. Rapp et al., *The Oncogene Handbook,* E. P. Reddy, A. M Skalka and T. Curran, eds., Elsevier Science Publishers, New York, 1988, pp. 213–253.

Oligonucleotides have been employed as therapeutic moieties in the treatment of disease states in animals and man. For example, workers in the field have now identified antisense, triplex and other oligonucleotide compositions which are capable of modulating expression of genes implicated in viral, fungal and metabolic diseases. Antisense oligonucleotides have been safely administered to humans and clinical trials of several antisense oligonucleotide drugs, targeted both to viral and cellular gene products, are presently underway. The phosphorothioate oligonucleotide drug, Vitravene™ (ISIS 2922), has been approved by the FDA for treatment of cytomegalovirus retinitis in AIDS patients. It is thus established that oligonucleotides can be useful therapeutic instrumentalities and can be configured to be useful in treatment regimes for treatment of cells and animal subjects, especially humans.

Antisense oligonucleotide inhibition of gene expression has proven to be a useful tool in understanding the roles of raf genes. An antisense oligonucleotide complementary to the first six codons of human c-raf has been used to demonstrate that the mitogenic response of T cells to interleukin-2 (IL-2) requires c-raf. Cells treated with the oligonucleotide showed a near-total loss of c-raf protein and a substantial reduction in proliferative response to IL-2. Riedel et al., *Eur. J. Immunol.* 1993, 23, 3146–3150. Rapp et al. have disclosed expression vectors containing a raf gene in an antisense orientation downstream of a promoter, and methods of inhibiting raf expression by expressing an antisense Raf gene or a mutated Raf gene in a cell. WO application 93/04170. An antisense oligodeoxyribonucleotide complementary to codons 1–6 of murine c-Raf has been used to abolish insulin stimulation of DNA synthesis in the rat hepatoma cell line H4IIE. Tornkvist et al., *J. Biol. Chem.* 1994, 269, 13919–13921. WO Application 93/06248 discloses methods for identifying an individual at increased risk of developing cancer and for determining a prognosis and proper treatment of patients afflicted with cancer comprising amplifying a region of the c-raf gene and analyzing it for evidence of mutation.

Denner et al. disclose antisense polynucleotides hybridizing to the gene for raf, and processes using them. WO 94/15645. Oligonucleotides hybridizing to human and rat raf sequences are disclosed.

Iversen et al. disclose heterotypic antisense oligonucleotides complementary to raf which are able to kill ras-activated cancer cells, and methods of killing raf-activated cancer cells. Numerous oligonucleotide sequences are disclosed, none of which are actually antisense oligonucleotide sequences.

There remains a long-felt need for improved compositions and methods for inhibiting raf gene expression.

SUMMARY OF THE INVENTION

The present invention provides oligonucleotides which are targeted to nucleic acids encoding human raf and are capable of inhibiting raf expression. The present invention also provides chimeric oligonucleotides targeted to nucleic acids encoding human raf. The oligonucleotides of the invention are believed to be useful both diagnostically and therapeutically, and are believed to be particularly useful in the methods of the present invention.

The present invention also comprises methods of inhibiting the expression of human raf, particularly the abnormal expression of raf. These methods are believed to be useful both therapeutically and diagnostically as a consequence of the association between raf expression and hyperproliferation. These methods are also useful as tools, for example for detecting and determining the role of raf expression in various cell functions and physiological processes and conditions and for diagnosing conditions associated with raf expression.

The present invention also comprises methods of inhibiting hyperproliferation of cells using oligonucleotides of the invention. These methods are believed to be useful, for example in diagnosing raf-associated cell hyperproliferation. These methods employ the oligonucleotides of the invention. These methods are believed to be useful both therapeutically and as clinical research and diagnostic tools.

DETAILED DESCRIPTION OF THE INVENTION

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation. The raf genes are members of a gene family which encode related proteins termed A-, B- and c-raf. Raf genes code for highly conserved serine-threonine-specific protein kinases. These enzymes are differentially expressed; c-raf, the most thoroughly characterized, is expressed in all organs and in all cell lines that have been examined. A- and B-raf are expressed in urogenital and brain tissues, respectively. c-raf protein kinase activity and subcellular distribution are regulated by mitogens via phosphorylation. Various growth factors, including epidermal growth factor, acidic fibroblast growth factor, platelet-derived growth factor, insulin, granulocyte-macrophage colony-stimulating factor, interleukin-2, interleukin-3 and erythropoietin, have been shown to induce phosphorylation of c-raf. Thus, c-raf is believed to play a fundamental role in the normal cellular signal transduction pathway, coupling a multitude of growth factors to their net effect, cellular proliferation.

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. Examples of abnormal proliferative conditions are hyperproliferative disorders such as cancers, tumors, hyperplasias, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

It has now been found that elimination or reduction of raf gene expression may halt or reverse abnormal cell proliferation. This has been found even in when levels of raf expression are not abnormally high. There is a great desire to provide compositions of matter which can modulate the expression of the raf gene. It is greatly desired to provide methods of detection of the raf gene in cells, tissues and animals. It is also desired to provide methods of diagnosis and treatment of abnormal proliferative conditions associated with abnormal raf gene expression. In addition, kits and reagents for detection and study of the raf gene are desired. "Abnormal" raf gene expression is defined herein as abnormally high levels of expression of the raf protein, or any level of raf expression in an abnormal proliferative condition or state.

The present invention employs oligonucleotides targeted to nucleic acids encoding raf. This relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding raf; in other words, the raf gene or mRNA expressed from the raf gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of raf gene expression is presently the preferred form of modulation. This modulation can be measured in ways which are routine in the art, for example by Northern blot assay of mRNA expression or Western blot assay of protein expression as taught in the examples of the instant application. Effects on cell proliferation or tumor cell growth can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In preferred embodiments of this invention, oligonucleotides are provided which are targeted to mRNA encoding c-raf, A-raf and B-raf. In accordance with this invention, persons of ordinary skill in the art will understand that mRNA includes not only the coding region which carries the information to encode a protein using the three letter genetic code, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the 5'- or 3'-untranslated region of the human c-raf mRNA. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with raf protein expression.

The present invention provides oligonucleotides for modulation of raf gene expression. Such oligonucleotides are targeted to nucleic acids encoding raf. oligonucleotides and methods for modulation of c-raf, A-raf and B-raf are presently preferred; however, compositions and methods for modulating expression of other forms of raf are also believed to have utility and are comprehended by this invention. As hereinbefore defined, “modulation” means either inhibition or stimulation. Inhibition of raf gene expression is presently the preferred form of modulation.

In the context of this invention, the term “oligonucleotide” refers to an oligomer or polymer of nucleotide or nucleoside monomers consisting of naturally occurring bases, sugars and intersugar (backbone) linkages. The term “oligonucleotide” also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

It is not necessary for all positions in a given compound to be uniformly modified, and in fact more than one of the aforementioned modifications may be incorporated in a single compound or even at a single nucleoside within an oligonucleotide. Certain preferred oligonucleotides of this invention are chimeric oligonucleotides. “Chimeric oligonucleotides” or “chimeras”, in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one preferred embodiment, a chimeric oligonucleotide comprises at least one region modified to increase target binding affinity, and, usually, a region that acts as a substrate for RNAse H. Affinity of an oligonucleotide for its target (in this case a nucleic acid encoding raf) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase raf mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of raf gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

The oligonucleotides in accordance with this invention preferably are from about 8 to about 50 nucleotides in length. In the context of this invention it is understood that this encompasses non-naturally occurring oligomers as hereinbefore described, having 8 to 50 monomers. Particularly preferred are antisense oligonucleotides comprising from about 8 to about 30 nucleobases (i.e. from about 8 to about 30 linked nucleosides).

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925;

5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (*Science,* 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. 5,602,240. Also preferred are oligonucleotides having morpholino backbone structures of the above-referenced U.S. Pat. 5,034,506.

Modified oligonucleotides may also contain one or more substituted sugar moieties. Preferred oligonucleotides comprise one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O-$CH_2CH_2OCH_3$, also known as 2'-O-(2-methoxyethyl) or 2'-MOE) (Martin et al., *Helv. Chim. Acta* 1995, 78, 486–504) i.e., an alkoxyalkoxy group. Further preferred modifications include 2'-dimethylaminooxyethoxy, i.e., a $O(CH_2)_2ON(CH_3)_2$ group, also known as 2'-DMAOE, and 2'-dimethylaminoethoxyethoxy (2'-DMAEOE) as described in examples hereinbelow.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 35 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.,* 1996, 277, 923–937)

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

It has now been found that certain oligonucleotides targeted to portions of the c-raf mRNA are particularly useful for inhibiting raf expression and for interfering with cell hyperproliferation. Methods for inhibiting c-raf expression using antisense oligonucleotides are, likewise, useful for interfering with cell hyperproliferation. In the methods of the invention, tissues or cells are contacted with oligonucleotides. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

For therapeutics, methods of inhibiting hyperproliferation of cells and methods of treating abnormal proliferative conditions are provided. The formulation of therapeutic compositions and their subsequent administration is believed to be within the skill in the art. In general, for therapeutics, a patient suspected of needing such therapy is given an oligonucleotide in accordance with the invention, commonly in a pharmaceutically acceptable carrier, in amounts and for periods which will vary depending upon the nature of the particular disease, its severity and the patient's overall condition. The pharmaceutical compositions of this invention may be administered in a number of ways depending upon whether local or systemic treatment is desired, and upon the area to be treated. Administration may be topical (including ophthalmic, vaginal, rectal, intranasal), oral, or parenteral, for example by intravenous drip, intravenous injection or subcutaneous, intraperitoneal, intraocular, intravitreal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is Lipofectin (BRL, Bethesda Md.).

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, teniposide, cisplatin, carboplatin, topotecan, irinotecan, gemcitabine and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Other drugs such as leucovorin, which is a form of folic acid used as a "rescue" after high doses of methotrexate or other folic acid agonists, may also be administered. In some embodiments, 5-FU and leucovorin are given in combination as an IV bolus with the compounds of the invention being provided as an IV infusion.

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be calculated based on EC50's in in vitro and in vivo animal studies. For example, given the molecular weight of compound (derived from oligonucleotide sequence and chemical structure) and an effective dose such as an IC50, for example (derived experimentally), a dose in mg/kg is routinely calculated.

The present invention is also suitable for diagnosing abnormal proliferative states in tissue or other samples from patients suspected of having a hyperproliferative disease such as cancer, psoriasis or blood vessel restenosis or atherosclerosis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. Similarly, the present invention can be used to distinguish raf-associated tumors from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of raf expression. For example, radiolabeled oligonucleotides can be prepared by $^{32}P$ labeling at the 5' end with polynucleotide kinase. Sambrook et al., *Molecular Cloning. A Laboratory Manual,* Cold Spring Harbor Laboratory Press, 1989, Volume 2, p. 10.59. Radiolabeled oligonucleotides are then contacted with tissue or cell samples suspected of raf expression and the sample is washed to remove unbound oligonucleotide. Radioactivity remaining in the sample indicates bound oligonucleotide (which in turn indicates the presence of raf) and can be quantitated using a scintillation counter or other routine means. Radiolabeled oligo can also be used to perform autoradiography of tissues to determine the localization, distribution and quantitation of raf expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing raf. Quantitation of the silver grains permits raf expression to be detected.

Analogous assays for fluorescent detection of raf expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va. See 1993 Catalog of Products for DNA Research, Glen Research, Sterling Va., p. 21).

Each of these assay formats is known in the art. One of skill could easily adapt these known assays for detection of raf expression in accordance with the teachings of the invention providing a novel and useful means to detect raf expression.

Oligonucleotide Inhibition of c-raf Expression

The oligonucleotides shown in Table 1 were designed using the Genbank c-raf sequence HSRAFR (Genbank accession no. x03484; SEQ ID NO: 64), synthesized and tested for inhibition of c-raf mRNA expression in T24 bladder carcinoma cells using a Northern blot assay. All are oligodeoxynucleotides with phosphorothioate backbones.

TABLE 1

Human c-raf Kinase Antisense Oligonucleotides

| Isis # | Sequence (5' → 3') | Site | SEQ ID NO: |
|---|---|---|---|
| 5000 | TGAAGGTGAGCTGGAGCCAT | Coding | 1 |
| 5074 | GCTCCATTGATGCAGCTTAA | AUG | 2 |
| 5075 | CCCTGTATGTGCTCCATTGA | AUG | 3 |
| 5076 | GGTGCAAAGTCAACTAGAAG | STOP | 4 |
| 5097 | ATTCTTAAACCTGAGGGAGC | 5'UTR | 5 |
| 5098 | GATGCAGCTTAAACAATTCT | 5'UTR | 6 |
| 5131 | CAGCACTGCAAATGGCTTCC | 3'UTR | 7 |
| 5132 | TCCCGCCTGTGACATGCATT | 3'UTR | 8 |
| 5133 | GCCGAGTGCCTTGCCTGGAA | 3'UTR | 9 |
| 5148 | AGAGATGCAGCTGGAGCCAT | Coding | 10 |
| 5149 | AGGTGAAGGCCTGGAGCCAT | Coding | 11 |
| 6721 | GTCTGGCGCTGCACCACTCT | 3'UTR | 12 |
| 6722 | CTGATTTCCAAAATCCCATG | 3'UTR | 13 |
| 6731 | CTGGGCTGTTTGGTGCCTTA | 3'UTR | 14 |
| 6723 | TCAGGGCTGGACTGCCTGCT | 3'UTR | 15 |

TABLE 1-continued

| Human c-raf Kinase Antisense Oligonucleotides | | | |
|---|---|---|---|
| Isis # | Sequence (5' → 3') | Site | SEQ ID NO: |
| 7825 | GGTGAGGGAGCGGGAGGCGG | 5'UTR | 16 |
| 7826 | CGCTCCTCCTCCCCGCGGCG | 5'UTR | 17 |
| 7827 | TTCGGCGGCAGCTTCTCGCC | 5'UTR | 18 |
| 7828 | GCCGCCCCAACGTCCTGTCG | 5'UTR | 19 |
| 7848 | TCCTCCTCCCCGCGGCGGGT | 5'UTR | 20 |
| 7849 | CTCGCCCGCTCCTCCTCCCC | 5'UTR | 21 |
| 7847 | CTGGCTTCTCCTCCTCCCCT | 3'UTR | 22 |
| 8034 | CGGGAGGCGGTCACATTCGG | 5'UTR | 23 |
| 8094 | TCTGGCGCTGCACCACTCTC | 3'UTR | 24 |

In a first round screen of oligonucleotides at concentrations of 100 nM or 200 nM, oligonucleotides 5074, 5075, 5132, 8034, 7826, 7827 and 7828 showed at least 50% inhibition of c-raf mRNA and these oligonucleotides are therefore preferred. Oligonucleotides 5132 and 7826 (SEQ ID NO: 8 and SEQ ID NO: 17) showed greater than about 90% inhibition and are more preferred. In additional assays, oligonucleotides 6721, 7848, 7847 and 8094 decreased c-raf mRNA levels by greater than 50%. These oligonucleotides are also preferred. Of these, 7847 (SEQ ID NO: 22) showed greater than about 90% inhibition of c-raf mRNA and is more preferred.

Specificity of ISIS 5132 for raf

Specificity of ISIS 5132 for raf mRNA was demonstrated by a Northern blot assay in which this oligonucleotide was tested for the ability to inhibit Ha-ras mRNA as well as c-raf mRNA in T24 cells. Ha-ras is a cellular oncogene which is implicated in transformation and tumorigenesis. ISIS 5132 was shown to abolish c-raf mRNA almost completely with no effect on Ha-ras mRNA levels.

2'-modified Oligonucleotides

Certain of these oligonucleotides were synthesized with either phosphodiester (P═O) or phosphorothioate (P═S) backbones and were also uniformly substituted at the 2' position of the sugar with either a 2'-O-methyl, 2'-O-propyl, or 2'-fluoro group. Oligonucleotides are shown in Table 2.

TABLE 2

| Uniformly 2' Sugar-modified c-raf Oligonucleotides | | | | |
|---|---|---|---|---|
| ISIS # | Sequence | Site | Modif | SEQ ID NO. |
| 6712 | TCCCGCCTGTGACATGCATT | 3'UTR | OMe/P = S | 8 |
| 8033 | CGGGAGGCGGTCACATTCGG | 5'UTR | OMe/P = S | 23 |
| 7829 | GGTGAGGGAGCGGGAGGCGG | 5'UTR | OMe/P = S | 16 |
| 7830 | CGCTCCTCCTCCCCGCGGCG | 5'UTR | OMe/P = S | 17 |
| 7831 | TTCGGCGGCAGCTTCTCGCC | 5'UTR | OMe/P = S | 18 |
| 7832 | GCCGCCCCAACGTCCTGTCG | 5'UTR | OMe/P = S | 19 |
| 7833 | ATTCTTAAACCTGAGGGAGC | 5'UTR | OMe/P = S | 5 |
| 7834 | GATGCAGCTTAAACAATTCT | 5'UTR | OMe/P = S | 6 |
| 7835 | GCTCCATTGATGCAGCTTAA | AUG | OMe/P = S | 2 |
| 7836 | CCCTGTATGTGCTCCATTGA | AUG | OMe/P = S | 3 |
| 8035 | CGGGAGGCGGTCACATTCGG | 5'UTR | OPr/P = O | 23 |
| 7837 | GGTGAGGGAGCGGGAGGCGG | 5'UTR | OPr/P = O | 16 |
| 7838 | CGCTCCTCCTCCCCGCGGCG | 5'UTR | OPr/P = O | 17 |
| 7839 | TTCGGCGGCAGCTTCTCGCC | 5'UTR | OPr/P = O | 18 |
| 7840 | GCCGCCCCAACGTCCTGTCG | 5'UTR | OPr/P = O | 19 |
| 7841 | ATTCTTAAACCTGAGGGAGC | 5'UTR | OPr/P = O | 5 |
| 7842 | GATGCAGCTTAAACAATTCT | 5'UTR | OPr/P = O | 6 |
| 7843 | GCTCCATTGATGCAGCTTAA | AUG | OPr/P = O | 2 |
| 7844 | CCCTGTATGTGCTCCATTCA | AUG | OPr/P = O | 3 |
| 9355 | CGGGAGGCGGTCACATTCGG | 5'UTR | 2'F/P = S | 23 |

Oligonucleotides from Table 2 having uniform 2'O-methyl modifications and a phosphorothioate backbone were tested for ability to inhibit c-raf protein expression in T24 cells as determined by Western blot assay. Oligonucleotides 8033, 7834 and 7835 showed the greatest inhibition and are preferred. Of these, 8033 and 7834 are more preferred.

Chimeric Oligonucleotides

Chimeric oligonucleotides having SEQ ID NO: 8 were prepared. These oligonucleotides had central "gap" regions of 6, 8, or 10 deoxynucleotides flanked by two regions of 2'-O-methyl modified nucleotides. Backbones were uniformly phosphorothioate. In Northern blot analysis, all three of these oligonucleotides (ISIS 6720, 6-deoxy gap; ISIS 6717, 8-deoxy gap; ISIS 6729, 10-deoxy gap) showed greater than 70% inhibition of c-raf mRNA expression in T24 cells. These oligonucleotides are preferred. The 8-deoxy gap compound (6717) showed greater than 90% inhibition and is more preferred.

Additional chimeric oligonucleotides were synthesized having one or more regions of 2'-O-methyl modification and uniform phosphorothioate backbones. These are shown in Table 3. All are phosphorothioates; bold regions indicate 2'-O-methyl modified regions.

TABLE 3

| Chimeric 2'-O-methyl P = S c-raf oligonucleotides | | | |
|---|---|---|---|
| Isis # | Sequence | Target site | SEQ ID NO: |
| 7848 | TCCTCCTCCCCGCGGCGGGT | 5'UTR | 20 |
| 7352 | **TCCTCCTCCCC**GCGGCGGGT | 5'UTR | 20 |
| 7849 | CTCGCCCGCTCCTCCTCCCC | 5'UTR | 21 |
| 7851 | CTCGCCCGC**TCCTCCTCCCC** | 5'UTR | 21 |
| 7856 | TTCTCGCCCGCTCCTCCTCC | 5'UTR | 25 |
| 7855 | **TTCTC**GCCCGCTCC**TCCTCC** | 5'UTR | 25 |
| 7854 | **TTCTCCTCCTCC**CCTGGCAG | 3'UTR | 26 |
| 7347 | CTGGCTTCTCCTCCTCCCCT | 3'UTR | 22 |
| 7850 | CTGGCT**TCTCCTCCTCCCCT** | 3'UTR | 22 |
| 7853 | CCTGCTGGC**TTCTCCTCCTC** | 3'UTR | 27 |

When tested for their ability to inhibit c-raf mRNA by Northern blot analysis, ISIS 7848, 7849, 7851, 7856, 7855, 7854, 7847, and 7853 gave better than 70% inhibition and are therefore preferred. Of these, 7851, 7855, 7847 and 7853 gave greater than 90% inhibition and are more preferred.

Additional chimeric oligonucleotides with various 2' modifications were prepared and tested. These are shown in Table 4. All are phosphorothioates; bold regions indicate 2'-modified regions.

TABLE 4

| Chimeric 2'-modified P = S c-raf oligonucleotides | | | | |
|---|---|---|---|---|
| Isis # | SEQUENCE | Target site | Modification | SEQ ID NO: |
| 6720 | **TCCCGCC**TGTGAC**ATGCATT** | 3'UTR | 2'-O-Me | 8 |
| 6717 | **TCCCGC**CTGTGACA**TGCATT** | 3'UTR | 2'-O-Me | 8 |
| 6729 | **TCCCG**CCTGTGACAT**GCATT** | 3'UTR | 2'-O-Me | 8 |
| 8097 | TCTGGCG**CTGCACCACTCTC** | 3'UTR | 2'-O-Me | 24 |
| 9270 | **TCCCGC**CTGTGACA**TGCATT** | 3'UTR | 2'-O-Pro | 8 |
| 9058 | **TCCCGC**CTGTGACA**TGCATT** | 3'UTR | 2'-F | 8 |
| 9057 | TCTGGCG**CTGCACCACTCTC** | 3'UTR | 2'-F | 24 |

Of these, oligonucleotides 6720, 6717, 6729, 9720 and 9058 are preferred. Oligonucleotides 6717, 6729, 9720 and 9058 are more preferred.

Two chimeric oligonucleotides with 2'-O-propyl sugar modifications and chimeric P═O/P═S backbones were also synthesized. These are shown in Table 5, in which italic regions indicate regions which are both 2'-modified and have phosphodiester backbones.

TABLE 5

Chimeric 2'-modified P = S/P = O c-raf oligonucleotides

| Isis # | Sequence | Target site | Modification | SEQ ID NO: |
|---|---|---|---|---|
| 9271 | *TCCCGCC*TGTGACA*TGCATT* | 3'UTR | 2'-O-Pro | 8 |
| 8096 | TCTGGCG*CTGCACCACTCTC* | 3'UTR | 2'-O-Pro | 24 |

Inhibition of Cancer Cell Proliferation

The phosphorothioate oligonucleotide ISIS 5132 was shown to inhibit T24 bladder cancer cell proliferation. Cells were treated with various concentrations of oligonucleotide in conjunction with lipofectin (cationic lipid which increases uptake of oligonucleotide). A dose-dependent inhibition of cell proliferation was demonstrated, as indicated in Table 6, in which "None" indicates untreated control (no oligonucleotide) and "Control" indicates treatment with negative control oligonucleotide. Results are shown as percent inhibition compared to untreated control.

TABLE 6

Inhibition of T24 Cell Proliferation by ISIS 5132

| Oligo conc. | None | Control | 5132 |
|---|---|---|---|
| 50 nM | 0 | +9% | 23% |
| 100 nM | 0 | +4% | 24% |
| 250 nM | 0 | 10% | 74% |
| 500 nM | 0 | 18% | 82% |

Effect of ISIS 5132 on T24 Human Bladder Carcinoma Tumors

Subcutaneous human T24 bladder carcinoma xenografts in nude mice were established and treated with ISIS 5132 and an unrelated control phosphorothioate oligonucleotide administered intraperitoneally three times weekly at a dosage of 25 mg/kg. In this preliminary study, ISIS 5132 inhibited tumor growth after eleven days by 35% compared to controls. Oligonucleotide-treated tumors remained smaller than control tumors throughout the course of the study.

Antisense Oligonucleotides Targeted to A-raf

It is believed that certain oligonucleotides targeted to portions of the A-raf mRNA and which inhibit A-raf expression will be useful for interfering with cell hyperproliferation. Methods for inhibiting A-raf expression using such antisense oligonucleotides are, likewise, believed to be useful for interfering with cell hyperproliferation.

The phosphorothioate deoxyoligonucleotides shown in Table 7 were designed and synthesized using the Genbank A-raf sequence HUMARAFIR (Genbank listing x04790; SEQ ID NO: 65).

TABLE 7

Oligonucleotides Targeted to Human A-raf

| Isis # | Sequence | Target site | SEQ ID NO: |
|---|---|---|---|
| 9060 | GTC AAG ATG GGC TGA GGT gg | 5' UTR | 28 |
| 9061 | CCA TCC CGG ACA GTC ACC AC | Coding | 29 |
| 9062 | ATG AGC TCC TCG CCA TCC AG | Coding | 30 |
| 9063 | AAT GCT GGT GGA ACT TGT AG | Coding | 31 |
| 9064 | CCG GTA CCC CAG GTT CTT CA | Coding | 32 |
| 9065 | CTG GGC AGT CTG CCG GGC CA | Coding | 33 |
| 9066 | CAC CTC AGC TGC CAT CCA CA | Coding | 34 |
| 9067 | GAG ATT TTG CTG AGG TCC GG | Coding | 35 |
| 9068 | GCA CTC CGC TCA ATC TTG GG | Coding | 36 |
| 9069 | CTA AGG CAC AAG GCG GGC TG | Stop | 37 |
| 9070 | ACG AAC ATT GAT TGG CTG GT | 3' UTR | 38 |
| 9071 | GTA TCC CCA AAG CCA AGA GG | 3' UTR | 39 |
| 10228 | CAT CAG GGC AGA GAC GAA CA | 3' UTR | 40 |

Oligonucleotides ISIS 9061, ISIS 9069 and ISIS 10228 were evaluated by Northern blot analysis for their effects on A-raf mRNA levels in A549, T24 and NHDF cells. All three oligonucleotides decreased A-raf RNA levels in a dose-dependent manner in all three cell types, with inhibition of greater than 50% at a 500 nM dose in all cell types. The greatest inhibition (88%) was achieved with ISIS 9061 and 9069 in T24 cells. These three oligonucleotides (ISIS 9061, 9069 and 10228) are preferred, with ISIS 9069 and 9061 being more preferred.

Identification of Oligonucleotides Targeted to Rat and Mouse c-raf

Many conditions which are believed to be mediated by raf kinase are not amenable to study in humans. For example, tissue graft rejection is a condition which is likely to be ameliorated by interference with raf expression; but, clearly, this must be evaluated in animals rather than human transplant patients. Another such example is restenosis. These conditions can be tested in animal models, however, such as the rat and mouse models used here.

Oligonucleotide sequences for inhibiting c-raf expression in rat and mouse cells were identified. Rat and mouse c-raf genes have regions of high homology; a series of oligonucleotides which target both rat and mouse c-raf mRNA sequence were designed and synthesized, using information gained from evaluation of oligonucleotides targeted to human c-raf. These oligonucleotides were screened for activity in mouse bEND cells and rat A-10 cells using Northern blot assays. The oligonucleotides (all phosphorothioates) are shown in Table 8.

TABLE 8

Oligonucleotides targeted to mouse and rat c-raf

| ISIS # | Target site | Sequence | SEQ ID NO: |
|---|---|---|---|
| 10705 | Coding | GGAACATCTGGAATTTGGTC | 41 |
| 10706 | Coding | GATTCACTGTGACTTCGAAT | 42 |
| 10707 | 3'UTR | GCTTCCATTTCCAGGGCAGG | 43 |
| 10708 | 3'UTR | AAGAAGGCAATATGAAGTTA | 44 |
| 10709 | 3'UTR | GTGGTGCCTGCTGACTCTTC | 45 |
| 10710 | 3'UTR | CTGGTGGCCTAAGAACAGCT | 46 |
| 10711 | AUG | GTATGTGCTCCATTGATGCA | 47 |
| 10712 | AUG | TCCCTGTATGTGCTCCATTG | 48 |
| 11060 | 5'UTR | ATACTTATACCTGAGGGAGC | 49 |
| 11061 | 5'UTR | ATGCATTCTGCCCCCAAGGA | 50 |
| 11062 | 3'UTR | GACTTGTATACCTCTGGAGC | 51 |
| 11063 | 3'UTR | ACTGGCACTGCACCACTGTC | 52 |

TABLE 8-continued

| Oligonucleotides targeted to mouse and rat c-raf | | | |
|---|---|---|---|
| ISIS # | Target site | Sequence | SEQ ID NO: |
| 11064 | 3'UTR | AAGTTCTGTAGTACCAAAGC | 53 |
| 11065 | 3'UTR | CTCCTGGAAGACAGATTCAG | 54 |

Oligonucleotides ISIS 11061 and 10707 were found to inhibit c-raf RNA levels by greater than 90% in mouse bEND cells at a dose of 400 nM. These two oligonucleotides inhibited raf RNA levels virtually entirely in rat A-10 cells at a concentration of 200 nM. The IC50 for ISIS 10707 was found to be 170 nM in mouse bEND cells and 85 nM in rat A-10 cells. The IC50 for ISIS 11061 was determined to be 85 nM in mouse bEND cells and 30 nM in rat A-10 cells.

Effect of ISIS-11061 on Endogenous c-raf mRNA Expression in Mice

Mice were injected intraperitoneally with ISIS 11061 (50 mg/kg) or control oligonucleotide or saline control once daily for three days. Animals were sacrificed and organs were analyzed for c-raf mRNA expression by Northern blot analysis. ISIS 11061 was found to decrease levels of c-raf mRNA in liver by approximately 70%. Control oligonucleotides had no effects on c-raf expression. The effect of ISIS 11061 was specific for c-raf; A-raf and G3PDH RNA levels were unaffected by oligonucleotide treatment.

Antisense Oligonucleotide to c-raf Increases Survival in Murine Heart Allograft Model To determine the therapeutic effects of the c-raf antisense oligonucleotide ISIS 11061 in preventing allograft rejection, this oligonucleotide was tested for activity in a murine vascularized heterotopic heart transplant model. Hearts from C57BI10 mice were transplanted into the abdominal cavity of C3H mice as primary vascularized grafts essentially as described by Isobe et al., *Circulation* 1991, 84, 1246–1255. Oligonucleotides were administered by continuous intravenous administration via a 7-day Alzet pump. The mean allograft survival time for untreated mice was 7.83±0.75 days(7, 7, 8, 8, 8, 9 days). Allografts in mice treated for 7 days with 20 mg/kg or 40 mg/kg ISIS 11061 all survived at least 11 days (11, 11, 12 days for 20 mg/kg dose and >11, >11, >11 days for the 40 mg/kg dose).

In a pilot study conducted in rats, hearts from Lewis rats were transplanted into the abdominal cavity of ACI rats. Rats were dosed with ISIS 11061 at 20 mg/kg for 7 days via Alzet pump. The mean allograft survival time for untreated rats was 8.86±0.69 days (8, 8, 9, 9, 9, 9, 10 days). In rats treated with oligonucleotide, the allograft survival time was 15.3±1.15 days (14, 16, 16 days).

Effects of Antisense Oligonucleotide Targeted to c-raf on Smooth Muscle Cell Proliferation Smooth muscle cell proliferation is a cause of blood vessel stenosis, for example in atherosclerosis and restenosis after angioplasty. Experiments were performed to determine the effect of ISIS 11061 on proliferation of A-10 rat smooth muscle cells. Cells in culture were grown with and without ISIS 11061 (plus lipofectin) and cell proliferation was measured 24 and 48 hours after stimulation with fetal calf serum. ISIS 11061 (500 nM) was found to inhibit serum-stimulated cell growth in a dose-dependent manner with a maximal inhibition of 46% and 75% at 24 hours and 48 hours, respectively. An IC50 value of 200 nM was obtained for this compound. An unrelated control oligonucleotide had no effect at doses up to 500 nM.

Effects of Antisense Oligonucleotides Targeted to c-raf on Restenosis in Rats

A rat carotid artery injury model of angioplasty restenosis has been developed and has been used to evaluate the effects on restenosis of antisense oligonucleotides targeted to the c-myc oncogene. Bennett et al., *J. Clin. Invest.* 1994, 93, 820–828. This model will be used to evaluate the effects of antisense oligonucleotides targeted to rat c-raf, particularly ISIS 11061, on restenosis. Following carotid artery injury with a balloon catheter, oligonucleotides are administered either by intravenous injection, continuous intravenous administration via Alzet pump, or direct administration to the carotid artery in a pluronic gel matrix as described by Bennett et al. After recovery, rats are sacrificed, carotid arteries are examined by microscopy and effects of treatment on luminal cross-sections are determined.

Effects of ISIS 5132 (Antisense Oligodeoxynucleotide Targeted to Human c-raf on Tumor Growth in Human Patients Two clinical trials were undertaken to test ISIS 5132 on a variety of human tumors. In one study the compound was administered by intravenous infusion over 2 hours. In the other trial the drug was administered by intravenous infusion over 21 days using a continuous pump.

Two patients, both of whom had demonstrated tumor progression with previous cytotoxic chemotherapy, exhibited long-term stable disease in response to ISIS 5132 treatment in the 2-hour infusion study (29 patients evaluated). In these responding patients levels of c-raf expression in peripheral blood cells paralleled clinical response. Six patients showed stabilization of disease of two months or greater in response to ISIS 5132 treatment in the 21-day continuous infusion study (34 patients evaluated). These results are discussed hereinbelow in Examples 13–15.

The invention is further illustrated by the following examples which are illustrations only and are not intended to limit the present invention to specific embodiments.

EXAMPLES

Example 1

Synthesis and Characterization of Oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl phosphoramidites were purchased from Applied Biosystems (Foster City, Calif.). For phosphorothioate oligonucleotides, the standard oxidation bottle was replaced by a 0.2 M solution of H-1,2-benzodithiole-3-one 1,1-dioxide in acetonitrile for the stepwise thiation of the phosphite linkages. The thiation cycle wait step was increased to 68 seconds and was followed by the capping step. 2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide. 2'-O-propyl oligonucleotides were prepared by a slight modification of this procedure.

2'-fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and their phosphorothioate analogs were judged from electrophoresis to be greater than 80% full length material.

Example 2

Northern Blot Analysis of Inhibition of c-raf mRNA Expression

The human urinary bladder cancer cell line T24 was obtained from the American Type Culture Collection (Rockville Md.). Cells were grown in McCoy's 5A medium with L-glutamine (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of Opti-MEM reduced-serum medium containing 2.5 μl DOTMA. Oligonucleotide with lipofectin was then added to the desired concentration. After 4 hours of treatment, the medium was replaced with McCoy's medium. Cells were harvested 24 to 72 hours after oligonucleotide treatment and RNA was isolated using a standard CsCl purification method. Kingston, R. E., in *Current Protocols in Molecular Biology,* (F. M. Ausubel, R. Brent, R. E. Kingston, D. D. Moore, J. A. Smith, J. G. Seidman and K. Strahl, eds.), John Wiley and Sons, NY. Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene, La Jolla, Calif.) and hybridized to random-primed $^{32}P$-labeled c-raf cDNA probe (obtained from ATCC) or G3PDH probe as a control. RNA was quantitated using a Phosphorimager (Molecular Dynamics, Sunnyvale, Calif.).

Example 3

Specific Inhibition of c-raf Kinase Protein Expression in T24 Cells

T24 cells were treated with oligonucleotide (200 nM) and lipofectin at T=0 and T=24 hours. Protein extracts were prepared at T=48 hours, electrophoresed on acrylamide gels and analyzed by Western blot using polyclonal antibodies against c-raf (UBI, Lake Placid, N.Y.) or A-raf (Transduction Laboratories, Knoxville, Tenn.). Radiolabeled secondary antibodies were used and raf protein was quantitated using a Phosphorimager (Molecular Dynamics, Sunnyvale Calif.).

Example 4

Antisense Inhibition of Cell Proliferation

T24 cells were treated on day 0 for two hours with various concentrations of oligonucleotide and lipofectin (50 nM oligonucleotide in the presence of 2 μg/ml lipofectin; 100 nM oligonucleotide and 2 μg/ml lipofectin; 250 nM oligonucleotide and 6 μg/ml lipofectin or 500 nM oligonucleotide and 10 μg/ml lipofectin). On day 1, cells were treated for a second time at desired oligonucleotide concentration for two hours. On day 2, cells were counted.

Example 5

Effect of ISIS 5132 on T24 Human Bladder Carcinoma Tumor Xenografts in Nude Mice $5\times10^6$ T24 cells were implanted subcutaneously in the right inner thigh of nude mice. Oligonucleotides (ISIS 5132 and an unrelated control phosphorothioate oligonucleotide suspended in saline) were administered three times weekly beginning on day 4 after tumor cell inoculation. A saline-only control was also given. Oligonucleotides were given by intraperitoneal injection. Oligonucleotide dosage was 25 mg/kg. Tumor size was measured and tumor volume was calculated on the eleventh, fifteenth and eighteenth treatment days.

Example 6

Diagnostic Assay for raf-associated Tumors Using Xenografts in Nude Mice

Tumors arising from raf expression are diagnosed and distinguished from other tumors using this assay. A biopsy sample of the tumor is treated, e.g., with collagenase or trypsin or other standard methods, to dissociate the tumor mass. $5\times10^6$ tumor cells are implanted subcutaneously in the inner thighs of two or more nude mice. Antisense oligonucleotide (e.g., ISIS 5132) suspended in saline is administered to one or more mice by intraperitoneal injection three times weekly beginning on day 4 after tumor cell inoculation. Saline only is given to a control mouse. Oligonucleotide dosage is 25 mg/kg. Tumor size is measured and tumor volume is calculated on the eleventh treatment day. Tumor volume of the oligonucleotide-treated mice is compared to that of the control mouse. The volume of raf-associated tumors in the treated mice are measurably smaller than tumors in the control mouse. Tumors arising from causes other than raf expression are not expected to respond to the oligonucleotides targeted to raf and, therefore, the tumor volumes of oligonucleotide-treated and control mice are equivalent.

Example 7

Detection of raf Expression

Oligonucleotides are radiolabeled after synthesis by $^{32}P$ labeling at the 5' end with polynucleotide kinase. Sambrook et al., *Molecular Cloning. A Laboratory Manual,* Cold Spring Harbor Laboratory Press, 1989, Volume 2, pg. 11.31–11.32. Radiolabeled oligonucleotides are contacted with tissue or cell samples suspected of raf expression, such as tumor biopsy samples or skin samples where psoriasis is suspected, under conditions in which specific hybridization can occur, and the sample is washed to remove unbound oligonucleotide. Radioactivity remaining in the sample indicates bound oligonucleotide and is quantitated using a scintillation counter or other routine means.

Radiolabeled oligonucleotides of the invention are also used in autoradiography. Tissue sections are treated with radiolabeled oligonucleotide and washed as described above, then exposed to photographic emulsion according to standard autoradiography procedures. The emulsion, when developed, yields an image of silver grains over the regions expressing raf. The extent of raf expression is determined by quantitation of the silver grains.

Analogous assays for fluorescent detection of raf expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling Va.). Incubation of oligonucleotide and biological sample is carried out as described for radiolabeled oligonucleotides except that instead of a scintillation counter, a fluorimeter or fluorescence microscope is used to detect the fluorescence which indicates raf expression.

Example 8

Effect of Oligonucleotide on Endogenous c-raf Expression

Mice were treated by intraperitoneal injection at an oligonucleotide dose of 50 mg/kg on days 1, 2 and 3. On day 4 animals were sacrificed and organs removed for c-raf mRNA assay by Northern blot analysis. Four groups of animals were employed: 1) no oligonucleotide treatment (saline); 2) negative control oligonucleotide ISIS 1082 (targeted to herpes simplex virus; 3) negative control oligonucleotide 4189 (targeted to mouse protein kinase C-α; 4) ISIS 11061 targeted to rodent c-raf.

Example 9

Cardiac Allograft Rejection Model

Hearts were transplanted into the abdominal cavity of rats or mice (of a different strain from the donor) as primary vascularized grafts essentially as described by Isobe et al., *Circulation* 1991, 84, 1246–1255. Oligonucleotides were administered by continuous intravenous administration via a 7-day Alzet pump. Cardiac allograft survival was monitored by listening for the presence of a second heartbeat in the abdominal cavity.

Example 10

Proliferation Assay Using Rat A-10 Smooth Muscle Cells

A10 cells were plated into 96-well plates in Dulbecco's modified Eagle medium (DMEM)+10% fetal calf serum and allowed to attach for 24 hours. Cells were made quiescent by the addition of DMEM+0.2% dialyzed fetal calf serum for an additional 24 hours. During the last 4 hours of quiescence, cells were treated with ISIS 11061+lipofectin (Gibco-BRL, Bethesda Md.) in serum-free medium. Medium was then removed, replaced with fresh medium and the cells were stimulated with 10% fetal calf serum. The plates were the placed into the incubator and cell growth was evaluated by MTS conversion to formozan (Promega cell proliferation kit) at 24 and 48 hours after serum stimulation. A control oligonucleotide, ISIS 1082 (an unrelated oligonucleotide targeted to herpes simplex virus), was also tested.

Example 11

Rat Carotid Artery Restenosis Model

This model has been described by Bennett et al., *J. Clin. Invest.* 1994, 93, 820–828. Intimal hyperplasia is induced by balloon catheter dilatation of the carotid artery of the rat. Rats are anesthetized and common carotid artery injury is induced by passage of a balloon embolectomy catheter distended with 20 ml of saline. Oligonucleotides are applied to the adventitial surface of the arterial wall in a pluronic gel solution. Oligonucleotides are dissolved in a 0.25% pluronic gel solution at 4° C. (F127, BASF Corp.) at the desired dose. 100 μl of the gel solution is applied to the distal third of the common carotid artery immediately after injury. Control rats are treated similarly with gel containing control oligonucleotide or no oligonucleotide. The neck wounds are closed and the animals allowed to recover. 14 days later, rats are sacrificed, exsanguinated and the carotid arteries fixed in situ by perfusion with paraformaldehyde and glutaraldehyde, excised and processed for microscopy. Cross-sections of the arteries are calculated.

In an alternative to the pluronic gel administration procedure, rats are treated by intravenous injection or continuous intravenous infusion (via Alzet pump) of oligonucleotide.

Example 12

Additional Oligonucleotides Targeted to Human c-raf Kinase

The oligonucleotides shown in Table 9 were designed using the Genbank c-raf sequence HSRAFR (Genbank accession no. x03484; SEQ ID NO: 64), synthesized and tested for inhibition of c-raf mRNA expression as described in Examples 1 and 2. All are oligodeoxynucleotides with phosphorothioate backbones and all are targeted to the 3' UTR of human c-raf.

TABLE 9

Human c-raf Kinase Antisense Oligonucleotides

| Isis # | Sequence (5' → 3') | SEQ ID NO |
|---|---|---|
| 11459 | TTGAGCATGGGGAATGTGGG | 55 |
| 11457 | AACATCAACATCCACTTGCG | 56 |
| 11455 | TGTAGCCAACAGCTGGGGCT | 57 |
| 11453 | CTGAGAGGGCTGAGATGCGG | 58 |
| 11451 | GCTCCTGGAAGACAAAATTC | 59 |
| 11449 | TGTGACTAGAGAAACAAGGC | 60 |
| 11447 | CAAGAAAACCTGTATTCCTG | 61 |
| 11445 | TTGTCAGGTGCAATAAAAAC | 62 |
| 11443 | TTAAAATAACATAATTGAGG | 63 |

Of these, ISIS 11459 and 11449 gave 38% and 31% inhibition of c-raf mRNA levels in this assay and are, therefore, preferred. ISIS 11451, 11445 and 11443 gave 18%, 11% and 7% inhibition of c-raf expression, respectively.

Example 13

Effect of Antisense Oligonucleotide Targeted to c-raf on Patients with Cancer—2 Hour Infusion Twenty-nine fully evaluable patients with a range of cancer types received ISIS 5132 as a two-hour infusion three times weekly for three weeks. Following a one-week treatment-free interval, treatment was resumed, and maintained as long as the patient remained free of tumor progression or significant toxicity. Doses were escalated from 0.5 to 6.0 mg/kg in cohorts of three patients. The drug was well-tolerated and no patient required dose reduction.

Patients with refractory malignancies received ISIS 5132 at 2-hour intravenous infusion three times weekly for 3 consecutive weeks at one of nine dose levels ranging from 0.5 mg/kg to 6.0 mg/kg. Eligibility required adequate bone marrow function (neutrophils≧1,5000/mm$^3$, hemoglobin≧9.0 g/dL, and platelets≧1000,000/mm$^3$), serum creatine<2.0 mg/dL, total bilirubin<2.0 mg/dL, aspartate aminotransferase<2 times upper normal limit (<5 times upper normal limit in the presence of liver metastases), and no prolongation of the prothrombin time (PT) or activated partial thromboplastin time (aPTT). Blood counts and biochemical profiles were performed twice weekly during the first week and once a week thereafter. ISIS 5132 was supplied as a sterile solution in vials containing 1.1 mL or 10.5 mL of phosphate-buffered saline at a concentration of 10 mg/mL. Prior to administration, ISIS 5132 was diluted in normal saline to a total volume of 50 mL and the infused intravenously over two hours. Following a one-week treatment-free interval, dosing was resumed and maintained as long as the patient remained free of tumor progression or significant toxicity.

Example 14

Reduction of c-raf Expression in Peripheral Blood Mononuclear Cells of Cancer Patients After Treatment with Antisense Oligonucleotide Peripheral-blood mononuclear cells (PBMCS) for c-raf mRNA analysis were collected at baseline and on days 3, 5, 8, and 15 of cycle 1 and on day 1 of each cycle thereafter. PBMCs were isolated by Ficoll-Hypaque density centrifugation and stored at −70° C. Total RNA was isolated using Trizol reagent (Gibco BRL, Rockville, Md.) according to the manufacturer's directions. Because of the low abundance of the c-raf message in PBMCs, mRNA quantitation was performed using a reverse-transcriptase polymerase chain reaction (RT-PCR) assay. 100 ng total RNA was used for each cDNA reaction. C-raf expression was normalized to that of the endogenous standard β-actin by calculating the ration of the radiolabeled PCR products. PCR reactions (25 μl total volume, containing 0.1–10 μl cDNA, 12.5 pmol of each of the c-raf or β-actin primers, and 1 μCi $\alpha$-$^{32}$P dCTP) were heated to 95° C. for 5 minutes then amplified for 28–36 cycles at 95° C. for 1 minute, 55° C. for 1 minute and 72° C. for 2 minutes. The products were loaded on 8% urea polyacrylamide gels which were then dried at 80° C. for 1 hour under vacuum and exposed to film for several hours at −80° C. Reductions in c-raf expression were identified in 13 of 14 patients within 48 hours of initial ISIS 5132 dosing. The median reduction was to 42% (mean 53%) of initial values (p=0.002). Compared to baseline values, median reduction in expression on day 5 was 26% (mean 71%; p=0.017), on day 8 32% (mean 81%; p=0.03), and on day 15 35% (mean 74%; p=0.017).

Clinical Responses in Cancer Patients—2 hr Infusion

Two patients, both of whom had demonstrated tumor progression with previous cytotoxic chemotherapy, exhibited long-term stable disease in response to ISIS 5132 treatment. One was a 68-year old man with colorectal cancer metastatic to liver who had progressed two years after adjuvant therapy with 5-fluorouracil/leucovorin, and had evinced further tumor growth during therapy with a 17-1A monoclonal antibody and irinotecan. Following treatment with 3 mg/kg of ISIS 5132, minor (20%) shrinkage in a liver metastasis was accompanied by a progressive decline in choreoembryonic antigen (CEA, a marker for colon cancer) from 895 ng/mL to 618 ng/mL. During this time, c-raf mRNA values declined to below 10% of the initial value. After seven cycles of treatment, both the plasma CEA values and the PBMC c-raf mRNA began to increase, and one month later a CT scan revealed progression of the hepatic metastases.

A 46-year old woman with renal cell cancer metastatic to lung and lymph nodes failed to respond to interleukin-2, α-interferon and 5-fluorouracil in combination, and began treatment with ISIS 5132 at 5 mg/kg. She had immediate symptomatic improvement, but the size of the tumor was unchanged on CT scans. After ten cycles of treatment, she began to have recurrent pain, and progression was identified radiologically. In this patient the nadir PBMC c-raf mRNA was 9%, and values remained low until the beginning of the ninth cycle, when a return above baseline was observed, again followed shortly thereafter by progressive disease.

Example 15

Effect of Antisense Oligonucleotide Targeted to c-raf on Patients with Cancer—21 Day Continuous Infusion A continuous intravenous infusion of ISIS 5132 was administered for 21 days every 4 weeks to 34 patients with a variety of solid tumors refractory to standard therapy. The dose of ISIS 5132 was increased in sequential cohorts of patients, as toxicity allowed, until a final dose of 5.0 mg/kg of body weight was reached.

Eligible patients had histologically-documented solid malignancies of measurable or evaluable status refractory to standard therapy or for whom no effective therapy existed. Patients were prescreened in regard to their medical history as described above with the addition of the measurement of complement split products prior to the first infusion of ISIS 5132, 4 and 24 hours after starting the infusion and, repeated on days 7, 14 and 21. Patients received sequential, ascending, multiple doses of ISIS 5132 administered as a continuous IV infusion for 21 consecutive days at a pump rate of 1.5 mL/hour followed by one week of rest (one cycle). The initial dose of ISIS 5231 was 0.5 mg/kg of body weight. Subsequent doses were 1.0, 1.5, 2.0, 3.0, 4.0, and 5.0 mg/kg. The total dose was added to 250 mL of normal saline and infused as described above.

Clinical Responses in Cancer Patients—22-day Infusion

Six patients showed stabilization of disease of two months or greater. Of these two patients had prolonged stabilization: one patient (treated at 1.5 mg/kg/day) with renal cell carcinoma remained stable for 9 months, and the other (treated at 4.0 mg/kg/day) with pancreatic cancer remained stable for 10 months. The most significant response occurred in a 57-year old female with ovarian cancer, treated at 3.0 mg/kg/day. Her CA-125 level (a marker for ovarian cancer) at the time of initial surgical resection was 3300 u/mL. Following resection and a brief course of taxol and platinum, her CA-125 level was reportedly normal, but began to markedly increase again within 8 months. She was then treated with a succession of systemic therapies, most of which achieved only a short term, modest decrease in CA-125 levels. At the time of initiation of ISIS 5132 infusions, her CA-125 level was 1490 u/mL. She was treated with 10 cycles of ISIS 5132 and achieved a 97% reduction in tumor marker levels.

Example 16

Effect of Antisense Oligonucleotide Targeted to c-raf (21 Day Infusion) in Combination with Other Chemotherapeutic Agents in Cancer Patients Fourteen patients with refractory cancers were given ISIS 5132 at doses of 1.0–3.0 mg/kg/day as a 21 day IV infusion in combination with 5-fluorouracil (425 mg/m$^2$) and Leucovorin (20 mg/m$^2$) as an IV bolus given on days 1–5 every 4 weeks. In this ongoing study, 8 patients have been treated at the 2.0 mg/kg/day dose level. Toxicities that occurred were not dose-limiting. Disease stabilization lasting at least 4 cycles occurred in 4 patients (2 renal cell, 1 colon, 1 pancreatic). Thus ISIS 5132 at a dose of 2 mg/kg/day is active and well tolerated in combination with 5-FU/LV on this schedule.

Example 17

Effect of Antisense Oligonucleotide Targeted to c-raf in Pig Branch Retinal Vein Occlusion Model of Ocular Neovascularization Angiogenesis, or neovascularization, is the formation of new capillaries from existing blood vessels. In adult organisms this process is typically controlled and short-lived, for example in wound repair and regeneration. Gaiso, M. L., 1999, *Medscape Oncology* 2(1), Medscape Inc. However, aberrant capillary growth can occur and this uncontrolled growth plays a causal and/or supportive role in many pathologic conditions such as tumor growth and metastasis. In the context of this invention "aberrant angiogenesis" refers to unwanted or uncontrolled angiogenesis. Angiogenesis inhibitors are being evaluated for use as antitumor drugs. Other diseases and conditions associated with angiogenesis include arthritis, cardiovascular diseases, skin conditions, and aberrant wound healing. Aberrant angiogenesis can also occur in the eye, causing loss of vision. Examples of ocular conditions involving aberrant angiogenesis include macular degeneration, diabetic retinopathy and retinopathy of prematurity. A pig model of ocular neovascularization, the branch retinal vein occlusion (BVO) model, is used to study ocular neovascularization. An antisense oligonucleotide targeted to pig c-raf, ISIS 107189 (CCACACCACTCATCTCATCT; SEQ ID NO: 66) was tested in this model.

Male farm pigs (8–10 kg) were subjected to branch retinal vein occlusions (BVO) by laser treatment in both eyes. The extent of BVO was determined by indirect opthalmoscopy after a 2 week period. Intravitreous injections (10 μM) of ISIS 107189 were started on the day of BVO induction and were repeated at weeks 2, 6, and 10 after BVO (Right eye—vehicle, Left eye—antisense molecule). Stereo fundus photography and fluorescein angiography were performed at baseline BVO and at weeks 1,6 and 12 following intravitreous injections. In addition capillary gel electrophoresis analysis of the eye sections containing sclera, choroid, and the retina were performed to determine antisense concentrations, and gross and microscopic evaluations were performed to determine eye histopathology.

The antisense oligonucleotide targeted to c-raf significantly inhibited the neovascularization response compared to vehicle-only injections (p=0.05).

Example 18

Oligonucleotide Inhibition of B-raf Expression

The oligonucleotides shown in Table 10 were designed using the Genbank B-raf sequence HUMBRAF (Genbank listings M95712;M95720;x54072), provided herein as SEQ ID NO: 67, synthesized and tested for inhibition of B-raf mRNA expression in T24 bladder carcinoma cells or A549 lung carcinoma cells using a Northern blot assay.

The human urinary bladder cancer cell line T24 and the human lung tumor cell line A549 were obtained from the American Type Culture Collection (Rockville Md.). T24 cells were grown in McCoy's 5A medium with L-glutamine and A549 cells were grown in DMEM low glucose medium (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of Opti-MEM reduced-serum medium containing 2.5 μl DOTMA per 100 nM oligonucleotide. Oligonucleotide with lipofectin was then added to the desired concentration. After 4 hours of treatment, the medium was replaced with appropriate medium (McCoy's or DMEM low glucose). Cells were harvested 24 to 72 hours after oligonucleotide treatment and RNA was isolated using a standard CsCl purification method. Kingston, R. E., in *Current Protocols in Molecular Biology,* (F. M. Ausubel, R. Brent, R. E. Kingston, D. D. Moore, J. A. Smith, J. G. Seidman and K. Strahl, eds.), John Wiley and Sons, NY. Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene, La Jolla, Calif.) and hybridized to a $^{32}$P-labeled B-raf cDNA probe or G3PDH probe as a control. The human B-raf cDNA probe was cloned by PCR using complementary oligonucleotide primers after reverse transcription of total RNA. Identity of the B-raf cDNA was confirmed by restriction digestion and direct DNA sequencing. RNA was quantitated using a Phosphorimager (Molecular Dynamics, Sunnyvale, Calif.).

TABLE 10

Human B-raf Kinase Antisense Oligonucleotides (All are phosphorothioate oligodeoxynucleotides)

| Isis # | Sequence (5' → 3') | Site | SEQ ID NO: |
|---|---|---|---|
| 13720 | ATTTTGAAGGAGACGGACTG | coding | 68 |
| 13721 | TGGATTTTGAAGGAGACGGA | coding | 69 |
| 13722 | CGTTAGTTAGTGAGCCAGGT | coding | 70 |
| 13723 | ATTTCTGTAAGGCTTTCACG | coding | 71 |
| 13724 | CCCGTCTACCAAGTGTTTTC | coding | 72 |
| 13725 | AATCTCCCAATCATCACTCG | coding | 73 |
| 13726 | TGCTGAGGTGTAGGTGCTGT | coding | 74 |
| 13727 | TGTAACTGCTGAGGTGTAGG | coding | 75 |
| 13728 | TGTCGTGTTTTCCTGAGTAC | coding | 76 |
| 13729 | AGTTGTGGCTTTGTGGAATA | coding | 77 |
| 13730 | ATGGAGATGGTGATACAAGC | coding | 78 |
| 13731 | GGATGATTGACTTGGCGTGT | coding | 79 |
| 13732 | AGGTCTCTGTGGATGATTGA | coding | 80 |
| 13733 | ATTCTGATGACTTCTGGTGC | coding | 81 |
| 13734 | GCTGTATGGATTTTTATCTT | coding | 82 |
| 13735 | TACAGAACAATCCCAAATGC | coding | 83 |
| 13736 | ATCCTCGTCCCACCATAAAA | coding | 84 |
| 13737 | CTCTCATCTCTTTTCTTTTT | coding | 85 |
| 13738 | GTCTCTCATCTCTTTTCTTT | coding | 86 |
| 13739 | CCGATTCAAGGAGGGTTCTG | coding | 87 |
| 13740 | TGGATGGGTGTTTTTGGAGA | coding | 88 |
| 13741 | CTGCCTGGATGGGTGTTTTT | coding | 89 |
| 14144 | GGACAGGAAACGCACCATAT | coding | 90 |
| 14143 | CTCATTTGTTTCAGTGGACA | stop codon | 91 |
| 14142 | TCTCTCACTCATTTGTTTCA | stop codon | 92 |
| 14141 | ACTCTCTCACTCATTTGTTT | stop codon | 93 |
| 14140 | GAACTCTCTCACTCATTTGT | coding | 94 |
| 14139 | TCCTGAACTCTCTCACTCAT | coding | 95 |
| 14138 | TTGCTACTCTCCTGAACTCT | coding | 96 |
| 14137 | TTTGTTGCTACTCTCCTGAG | coding | 97 |
| 14136 | CTTTTGTTGCTACTCTCCTG | coding | 98 |
| 13742 | GCTACTCTCCTGAACTCTCT | coding | 99 |
| 14135 | TTCCTTTTGTTGCTACTCTC | coding | 100 |
| 14134 | ATTTATTTTCCTTTTGTTGC | coding | 101 |
| 14133 | ATATGTTCATTTATTTTCCT | coding | 102 |
| 13743 | TTTATTTTCCTTTTGTTGCT | coding | 103 |
| 13744 | TGTTCATTTATTTTCCTTTT | coding | 104 |
| 14132 | ATTTAACATATAAGCAAACA | coding | 105 |
| 14529 | CTGCCTGGTACCCTGTTTTT | 5 mismatch | 106 |
| 14530 | CTGCCTGGAAGGGTGTTTTT | 1 mismatch | 107 |
| 14531 | CTGCCTGGTACGGTGTTTTT | 3 mismatch | 108 |

There are multiple B-raf transcripts. The two most prevalent transcripts were quantitated after oligonucleotide treatment. These transcripts run at approximately 8.5 kb (upper transcript) and 4.7 kb (lower transcript) under the gel conditions used. Both transcripts are translated into B-raf protein in cells. In the initial screen, A549 cells were treated with oligonucleotides at a concentration of 200 nM oligonucleotide for four hours in the presence of lipofectin. Results were normalized and expressed as a percent of control. In this initial screen, oligonucleotides giving a reduction of either B-raf mRNA transcript of approximately 30% or greater were considered active. According to this criterion, oligonucleotides 13722, 13724, 13726, 13727, 13728, 13730, 13732, 13733, 13736, 13739, 13740, 13741, 13742, 13743, 14135, 14136, 14138 and 14144 were found to be active. These sequences are therefore preferred. Of these, oligonucleotides 13727, 13730, 13740, 13741, 13743 and 14144 showed 40–50% inhibition of one or both B-raf transcripts in at least one assay. These sequences are therefore more preferred. In one of the two assays, ISIS 14144 reduced levels of both transcripts by 50–60% and ISIS 13741 reduced both transcripts by 65–70%. These two sequences are therefore highly preferred.

Dose response experiments were done in both T24 cells and A549 cells for the two most active oligonucleotides, ISIS 13741 and ISIS 14144 (SEQ ID NO: 89 and 90), along with mismatch control sequences having 1, 3 or 5 mismatches of the ISIS 13741 sequence. ISIS 13741 and 14144 had almost identical activity in this assay when the upper B-raf transcript was measured, with IC50s between 250 and 300 nM. The mismatch controls had no activity (ISIS 14531) or slight activity, with a maximum inhibition of less than 20% at the 400 nM dose (ISIS 14530, ISIS 14529). Against the lower B-raf transcript, ISIS 13741 and ISIS 14144 had IC50s of approximately 350 and 275 nM, respectively in this assay, with the mismatch controls never achieving 50% inhibition at concentrations up to 400 nM. Therefore, ISIS 13741 and 14144 are preferred.

Reduction of B-raf mRNA levels was measured in T24 cells by these oligonucleotides (all are phosphorothioate oligodeoxynucleotides) after a 4-hour treatment in the presence of lipofectin. Results are normalized to G3PDH and expressed as a percent of control. Against the upper transcript, ISIS 13741 and 14144 were again most active, with IC50s of approximately 100 nM and 275 nM, respectively, in this assay. The mismatch controls 14529 and 14531 had no activity, and the mismatch control 14530 achieved a maximum reduction of raf mRNA of approximately 20% at a 400 nM dose. Against the lower transcript, ISIS 13741 had an IC50 of approximately 100–125 nM and ISIS 14144 had an IC50 of approximately 250 nM in this assay, with the mismatch controls completely inactive. Therefore ISIS 13741 and 14144 are preferred.

2'-Methoxyethoxy (2'-MOE) Oligonucleotides Targeted to B-raf

The oligonucleotides shown in Table 11 were synthesized. Nucleotides shown in bold are 2'-MOE. 2'-MOE cytosines are all 5-methylcytosines. For backbone linkage, "s" indicates phosphorothioate (P═S) and "o" indicates phosphodiester (P═O).

TABLE 11

2'-MOE oligonucleotides targeted to human B-raf (bold = 2'-MOE)

| ISIS# | Sequence/modification | SEQ ID NO: |
|---|---|---|
| 13741 | CsTsGsCsCsTsGsGsAsTsGsGsGsTsGsTsTsTsTsT | 89 |
| 15339 | **CsTsGsCsCsTsGsGsAsTsGs**GsGsTsGsTsTsTsTsT | 89 |
| 15340 | **CoToGoCoCoToGoGoAoToGs**GsGsTsGsTsTsTsTsT | 89 |
| 15341 | **CsTsGsCsCs**TsGsGsAsTsGsGsGsTs**GsTsTsTsTsT** | 89 |
| 15342 | **CoToGoCoCs**TsGsGsAsTsGsGsGsTs**GoToToToToT** | 89 |
| 15343 | CsTsGsCsCsTsGsGsAs**ToGoGoGoToGoToToToToT** | 89 |
| 15344 | CsTsGsCsCsTsGsGsAs**TsGsGsGsTsGsTsTsTsTsT** | 89 |

These oligonucleotides were tested for their ability to reduce B-raf mRNA levels in T24 cells. Against the lower transcript, ISIS 13741 (P═S deoxy) and ISIS 15344 (P═S deoxy/MOE) had IC50s of approximately 250 nM. The other two compounds tested, ISIS 15341 and 15342, did not achieve 50% inhibition at doses up to 400 nM. Against the upper transcript, ISIS 13741 and 15344 demonstrated IC50s of approximately 150 nM, ISIS 15341 demonstrated an IC50 of approximately 200 nM and ISIS 15342 did not achieve 50% reduction at doses up to 400 nM. Based on these results, ISIS 15341, 13741 and 15344 are preferred.

What is claimed is:

1. A method of treating pancreatic, renal cell, colon or bladder cancer comprising administering to a human or cells thereof a therapeutically effective amount of an oligonucleotide 8 to 50 nucleotides in length which is targeted to mRNA encoding human c-raf (SEQ ID NO: 64), wherein said oligonucleotide comprises SEQ ID NO: 8.

2. The method of claim 1 comprising administering an oligonucleotide comprising SEQ ID NO: 8 in combination with a chemotherapeutic agent.

* * * * *

SEQUENCE LISTING

<160> NUMBER OF SEQ ID NOS: 108

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
tgaaggtgag ctggagccat 20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gctccattga tgcagcttaa 20

<210> SEQ ID NO 3
<211> LENGTH: 20
<212> TYPE: DNA
<213> ORGANISM: Artificial Sequence
<220> FEATURE:
<223> OTHER INFORMATION: Synthetic -continued

<400> SEQUENCE: 3
ccctgtatgt gctccattga 20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
ggtgcaaagt caactagaag 20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
attcttaaac ctgagggagc 20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gatgcagctt aaacaattct 20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cagcactgca aatggcttcc 20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tcccgcctgt gacatgcatt 20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
gccgagtgcc ttgcctggaa 20

<210> SEQ ID NO 10

-continued

<211> LENGTH: 20
<212> TYPE: DNA
<213> ORGANISM: Artificial Sequence
<220> FEATURE:
<223> OTHER INFORMATION: Synthetic

<400> SEQUENCE: 10
agagatgcag ctggagccat 20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
aggtgaaggc ctggagccat 20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
gtctggcgct gcaccactct 20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ctgatttcca aaatcccatg 20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
ctgggctgtt tggtgcctta 20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tcagggctgg actgcctgct 20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16

-continued ggtgagggag cgggaggcgg 20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
cgctcctcct ccccgcggcg 20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ttcggcggca gcttctcgcc 20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
gccgccccaa cgtcctgtcg 20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tcctcctccc cgcggcgggt 20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
ctcgcccgct cctcctcccc 20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ctggcttctc ctcctcccct 20

<210> SEQ ID NO 23
<211> LENGTH: 20
<212> TYPE: DNA

```
<213> ORGANISM: Artificial Sequence
<220> FEATURE:
<223> OTHER INFORMATION: Synthetic

<400> SEQUENCE: 23

cgggaggcgg tcacattcgg                                                20


<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24

tctggcgctg caccactctc                                                20


<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25

ttctcgcccg ctcctcctcc                                                20


<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26

ttctcctcct cccctggcag                                                20


<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27

cctgctggct tctcctcctc                                                20


<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28

gtcaagatgg gctgaggtgg                                                20


<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29

ccatcccgga cagtcaccac                                                20
```

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
atgagctcct cgccatccag 20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
aatgctggtg gaacttgtag 20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
ccggtacccc aggttcttca 20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
ctgggcagtc tgccgggcca 20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
cacctcagct gccatccaca 20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
gagattttgc tgaggtccgg 20

<210> SEQ ID NO 36
<211> LENGTH: 20
<212> TYPE: DNA
<213> ORGANISM: Artificial Sequence
<220> FEATURE:

-continued

<223> OTHER INFORMATION: Synthetic

<400> SEQUENCE: 36
gcactccgct caatcttggg 20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
ctaaggcaca aggcgggctg 20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
acgaacattg attggctggt 20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gtatccccaa agccaagagg 20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
catcagggca gagacgaaca 20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
ggaacatctg gaatttggtc 20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
gattcactgt gacttcgaat 20

```
<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43

gcttccattt ccagggcagg                                                   20


<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44

aagaaggcaa tatgaagtta                                                   20


<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45

gtggtgcctg ctgactcttc                                                   20


<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46

ctggtggcct aagaacagct                                                   20


<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47

gtatgtgctc cattgatgca                                                   20


<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48

tccctgtatg tgctccattg                                                   20


<210> SEQ ID NO 49
<211> LENGTH: 20
<212> TYPE: DNA
<213> ORGANISM: Artificial Sequence
<220> FEATURE:
<223> OTHER INFORMATION: Synthetic
```

<400> SEQUENCE: 49
atacttatac ctgagggagc 20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
atgcattctg cccccaagga 20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
gacttgtata cctctggagc 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
actggcactg caccactgtc 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
aagttctgta gtaccaaagc 20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
ctcctggaag acagattcag 20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
ttgagcatgg ggaatgtggg 20

<210> SEQ ID NO 56
<211> LENGTH: 20

-continued

<212> TYPE: DNA
<213> ORGANISM: Artificial Sequence
<220> FEATURE:
<223> OTHER INFORMATION: Synthetic

<400> SEQUENCE: 56
aacatcaaca tccacttgcg 20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
tgtagccaac agctggggct 20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
ctgagagggc tgagatgcgg 20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gctcctggaa gacaaaattc 20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
tgtgactaga gaaacaaggc 20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
caagaaaacc tgtattcctg 20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62

```
ttgtcaggtg caataaaaac                                              20


<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63

ttaaaataac ataattgagg                                              20


<210> SEQ ID NO 64
<211> LENGTH: 2977
<212> TYPE: DNA
<213> ORGANISM: Homo sapiens

<400> SEQUENCE: 64

ccgaatgtga ccgcctcccg ctccctcacc cgccgcgggg aggaggagcg ggcgagaagc     60

tgccgccgaa cgacaggacg ttggggcggc ctggctccct caggtttaag aattgtttaa    120

gctgcatcaa tggagcacat acagggagct tggaagacga tcagcaatgg ttttggattc    180

aaagatgccg tgtttgatgg ctccagctgc atctctccta caatagttca gcagtttggc    240

tatcagcgcc gggcatcaga tgatggcaaa ctcacagatc cttctaagac aagcaacact    300

atccgtgttt tcttgccgaa caagcaaaga acagtggtca atgtgcgaaa tggaatgagc    360

ttgcatgact gccttatgaa agcactcaag gtgaggggcc tgcaaccaga gtgctgtgca    420

gtgttcagac ttctccacga acacaaaggt aaaaaagcac gcttagattg gaatactgat    480

gctgcgtctt tgattggaga agaacttcaa gtagatttcc tggatcatgt tcccctcaca    540

acacacaact ttgctcggaa gacgttcctg aagcttgcct tctgtgacat ctgtcagaaa    600

ttcctgctca atggatttcg atgtcagact tgtggctaca aatttcatga gcactgtagc    660

accaaagtac ctactatgtg tgtggactgg agtaacatca gacaactctt attgtttcca    720

aattccacta ttggtgatag tggagtccca gcactacctt ctttgactat gcgtcgtatg    780

cgagagtctg tttccaggat gcctgttagt tctcagcaca gatattctac acctcacgcc    840

ttcaccttta acacctccag tccctcatct gaaggttccc tctcccagag gcagaggtcg    900

acatccacac ctaatgtcca catggtcagc accacgctgc ctgtggacag caggatgatt    960

gaggatgcaa ttcgaagtca cagcgaatca gcctcacctt cagccctgtc cagtagcccc   1020

aacaatctga gcccaacagg ctggtcacag ccgaaaaccc ccgtgccagc acaaagagag   1080

cgggcaccag tatctgggac ccaggagaaa aacaaaatta ggcctcgtgg acagagagat   1140

tcaagctatt attgggaaat agaagccagt gaagtgatgc tgtccactcg gattgggtca   1200

ggctcttttg gaactgttta taagggtaaa tggcacggag atgttgcagt aaagatccta   1260

aaggttgtcg acccaacccc agagcaattc caggccttca ggaatgaggt ggctgttctg   1320

cgcaaaacac ggcatgtgaa cattctgctt ttcatggggt acatgacaaa ggacaacctg   1380

gcaattgtga cccagtggtg cgagggcagc agcctctaca aacacctgca tgtccaggag   1440

accaagtttc agatgttcca gctaattgac attgcccggc agacggctca gggaatggac   1500

tatttgcatg caaagaacat catccataga gacatgaaat ccaacaatat atttctccat   1560

gaaggcttaa cagtgaaaat tggagatttt ggtttggcaa cagtaaagtc acgctggagt   1620

ggttctcagc aggttgaaca acctactggc tctgtcctct ggatggcccc agaggtgatc   1680

cgaatgcagg ataacaaccc attcagtttc cagtcggatg tctactccta tggcatcgta   1740
```

-continued ttgtatgaac tgatgacggg ggagcttcct tattctcaca tcaacaaccg agatcagatc 1800
atcttcatgg tgggccgagg atatgcctcc ccagatctta gtaagctata taagaactgc 1860
cccaaagcaa tgaagaggct ggtagctgac tgtgtgaaga aagtaaagga agagaggcct 1920
ctttttcccc agatcctgtc ttccattgag ctgctccaac actctctacc gaagatcaac 1980
cggagcgctt ccgagccatc cttgcatcgg gcagcccaca ctgaggatat caatgcttgc 2040
acgctgacca cgtccccgag gctgcctgtc ttctagttga ctttgcacct gtcttcaggc 2100
tgccagggga ggaggagaag ccagcaggca ccacttttct gctccctttc tccagaggca 2160
gaacacatgt tttcagagaa gctctgctaa ggaccttcta gactgctcac agggccttaa 2220
cttcatgttg ccttcttttc tatccctttg ggccctggga gaaggaagcc atttgcagtg 2280
ctggtgtgtc ctgctccctc cccacattcc ccatgctcaa ggcccagcct tctgtagatg 2340
cgcaagtgga tgttgatggt agtacaaaaa gcaggggccc agccccagct gttggctaca 2400
tgagtattta gaggaagtaa ggtagcaggc agtccagccc tgatgtggag acacatggga 2460
ttttggaaat cagcttctgg aggaatgcat gtcacaggcg ggactttctt cagagagtgg 2520
tgcagcgcca gacattttgc acataaggca ccaaacagcc caggactgcc gagactctgg 2580
ccgcccgaag gagcctgctt tggtactatg gaacttttct taggggacac gtcctccttt 2640
cacagcttct aaggtgtcca gtgcattggg atggttttcc aggcaaggca ctcggccaat 2700
ccgcatctca gccctctcag gagcagtctt ccatcatgct gaattttgtc ctccaggagc 2760
tgcccctatg gggcgggccg cagggccagc ctgtttctct aacaaacaaa caaacaaaca 2820
gccttgtttc tctagtcaca tcatgtgtat acaaggaagc caggaataca ggttttcttg 2880
atgatttggg ttttaatttt gtttttattg cacctgacaa aatacagtta tctgatggtc 2940
cctcaattat gttattttaa taaaataaat taaattt 2977

<210> SEQ ID NO 65
<211> LENGTH: 2458
<212> TYPE: DNA
<213> ORGANISM: Homo sapiens
<220> FEATURE:
<221> NAME/KEY: misc_feature
<222> LOCATION: (1088)..(1088)
<223> OTHER INFORMATION: n=a, c, g or t

<400> SEQUENCE: 65
tgacccaata agggtggaag gctgagtccc gcagagccaa taacgagagt ccgagaggcg 60
acggaggcgg actctgtgag gaaacaagaa gagaggccca agatggagac ggcggcggct 120
gtagcggcgt gacaggagcc ccatggcacc tgcccagccc cacctcagcc catcttgaca 180
aaatctaagg ctccatggag ccaccacggg gccccccctgc caatggggcc gagccatccc 240
gggcagtggg caccgtcaaa gtatacctgc ccaacaagca acgcacggtg gtgactgtcc 300
gggatggcat gagtgtctac gactctctag acaaggccct gaaggtgcgg ggtctaaatc 360
aggactgctg tgtggtctac cgactcatca agggacgaaa gacggtcact gcctgggaca 420
cagccattgc tcccctggat ggcgaggagc tcattgtcga ggtccttgaa gatgtcccgc 480
tgaccatgca caattttgta cggaagacct tcttcagcct ggcgttctgt gacttctgcc 540
ttaagtttct gttccatggc ttccgttgcc aaacctgtgg ctacaagttc caccagcatt 600
gttcctccaa ggtccccaca gtctgtgttg acatgagtac caaccgccaa cagttctacc 660
acagtgtcca ggatttgtcc ggaggctcca gacagcatga ggctccctcg aaccgccccc 720

-continued

```
tgaatgagtt gctaaccccc cagggtccca gcccccgcac ccagcactgt gacccggagc    780
acttcccctt ccctgcccca gccaatgccc ccctacagcg catccgctcc acgtccactc    840
ccaacgtcca tatggtcagc accacggccc ccatggactc caacctcatc cagctcactg    900
gccagagttt cagcactgat gctgccggta gtagaggagg tagtgatgga accccccggg    960
ggagccccag cccagccagc gtgtcctcgg ggaggaagtc cccacattcc aagtcaccag   1020
cagagcagcg cgagcggaag tccttggccg atgacaagaa gaaagtgaag aacctggggt   1080
accgggantc aggctattac tgggaggtac cacccagtga ggtgcagctg ctgaagagga   1140
tcgggacggg ctcgtttggc accgtgtttc gagggcggtg gcatggcgat gtggccgtga   1200
aggtgctcaa ggtgtcccag cccacagctg agcaggccca ggctttcaag aatgagatgc   1260
aggtgctcag gaagacgcga catgtcaaca tcttgctgtt tatgggcttc atgacccggc   1320
cgggatttgc catcatcaca cagtggtgtg agggctccag cctctaccat cacctgcatg   1380
tggccgacac acgcttcgac atggtccagc tcatcgacgt ggcccggcag actgcccagg   1440
gcatggacta cctccatgcc aagaacatca tccaccgaga tctcaagtct aacaacatct   1500
tcctacatga ggggctcacg gtgaagatcg gtgactttgg cttggccaca gtgaagactc   1560
gatggagcgg ggcccagccc ttggagcagc cctcaggatc tgtgctgtgg atggcagctg   1620
aggtgatccg tatgcaggac ccgaacccct acagcttcca gtcagacgtc tatgcctacg   1680
gggttgtgct ctacgagctt atgactggct cactgcctta cagccacatt ggctgccgtg   1740
accagattat ctttatggtg ggccgtggct atctgtcccc ggacctcagc aaaatctcca   1800
gcaactgccc caaggccatg cggcgcctgc tgtctgactg cctcaagttc cagcgggagg   1860
agcggcccct cttcccccag atcctggcca caattgagct gctgcaacgg tcactcccca   1920
agattgagcg gagtgcctcg gaaccctcct tgcaccgcac ccaggccgat gagttgcctg   1980
cctgcctact cagcgcagcc cgccttgtgc cttaggcccc gcccaagcca ccagggagcc   2040
aatctcagcc ctccacgcca aggagccttg cccaccagcc aatcaatgtt cgtctctgcc   2100
ctgatgctgc ctcaggatcc cccattcccc accctgggag atgagggggt ccccatgtgc   2160
ttttccagtt cttctggaat tgggggaccc ccgccaaaga ctgagccccc tgtctcctcc   2220
atcatttggt ttcctcttgg ctttggggat acttctaaat tttgggagct cctccatctc   2280
caatggctgg gatttgtggc agggattcca ctcagaacct ctctggaatt tgtgcctgat   2340
gtgccttcca ctggattttg ggggttccag caccccatgt ggattttggg gggtcccttt   2400
tgtgtctccc ccgccattca aggactcctc tctttcttca ccaagaagca cagaattc     2458
```

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66

```
ccacaccact catctcatct                                                 20
```

<210> SEQ ID NO 67
<211> LENGTH: 2510
<212> TYPE: DNA
<213> ORGANISM: Homo sapiens

<400> SEQUENCE: 67

```
agcctcccgg ccccctcccc gcccgacagc ggccgctcgg gccccggctc tcggttataa     60
```

-continued

```
gatggcggcg ctgagcggtg gcggtggtgg cggcgcggag ccgggccagg ctctgttcaa    120
cggggacatg gagcccgagg ccggcgccgg ccggcccgcg gcctcttcgg ctgcggaccc    180
tgccattccg gaggaggtgt ggaatatcaa acaaatgatt aagttgacac aggaacatat    240
agaggcccta ttggacaaat ttggtgggga gcataatcca ccatcaatat atctggaggc    300
ctatgaagaa tacaccagca agctagatgc actccaacaa agagaacaac agttattgga    360
atctctgggg aacggaactg atttttctgt ttctagctct gcatcaatgg ataccgttac    420
atcttcttcc tcttctagcc tttcagtgct accttcatct ctttcagttt ttcaaaatcc    480
cacagatgtg gcacggagca accccaagtc accacaaaaa cctatcgtta gagtcttcct    540
gcccaacaaa cagaggacag tggtacctgc aaggtgtgga gttacagtcc gagacagtct    600
aaagaaagca ctgatgatga gaggtctaat cccagagtgc tgtgctgttt acagaattca    660
ggatggagag aagaaaccaa ttggttggga cactgatatt tcctggctta ctggagaaga    720
attgcatgtg gaagtgttgg agaatgttcc acttacaaca cacaactttg tacgaaaaac    780
gtttttcacc ttagcatttt gtgacttttg tcgaaagctg cttttccagg gtttccgctg    840
tcaaacatgt ggttataaat ttcaccagcg ttgtagtaca gaagttccac tgatgtgtgt    900
taattatgac caacttgatt tgctgtttgt ctccaagttc tttgaacacc acccaatacc    960
acaggaagag gcgtccttag cagagactgc cctaacatct ggatcatccc cttccgcacc   1020
cgcctcggac tctattgggc cccaaattct caccagtccg tctccttcaa aatccattcc   1080
aattccacag cccttccgac cagcagatga agatcatcga aatcaatttg ggcaacgaga   1140
ccgatcctca tcagctccca atgtgcatat aaacacaata gaacctgtca atattgatga   1200
cttgattaga gaccaaggat ttcgtggtga tggaggatca accacaggtt tgtctgctac   1260
ccccccctgcc tcattacctg gctcactaac taacgtgaaa gccttacaga aatctccagg   1320
acctcagcga gaaaggaagt catcttcatc ctcagaagac aggaatcgaa tgaaaacact   1380
tggtagacgg gactcgagtg atgattggga gattcctgat gggcagatta cagtgggaca   1440
aagaattgga tctggatcat ttggaacagt ctacaaggga aagtggcatg gtgatgtggc   1500
agtgaaaatg ttgaatgtga cagcacctac acctcagcag ttacaagcct tcaaaaatga   1560
agtaggagta ctcaggaaaa cacgacatgt gaatatccta ctcttcatgg gctattccac   1620
aaagccacaa ctggctattg ttacccagtg gtgtgagggc tccagcttgt atcaccatct   1680
ccatatcatt gagaccaaat ttgagatgat caaacttata gatattgcac gacagactgc   1740
acagggcatg gattacttac acgccaagtc aatcatccac agagacctca agagtaataa   1800
tatatttctt catgaagacc tcacagtaaa aataggtgat tttggtctag ctacagtgaa   1860
atctcgatgg agtgggtccc atcagtttga acagttgtct ggatccattt tgtggatggc   1920
accagaagtc atcagaatgc aagataaaaa tccatacagc tttcagtcag atgtatatgc   1980
atttgggatt gttctgtatg aattgatgac tggacagtta ccttattcaa acatcaacaa   2040
cagggaccag ataattttta tggtgggacg aggatacctg tctccagatc tcagtaaggt   2100
acggagtaac tgtccaaaag ccatgaagag attaatggca gagtgcctca aaaagaaaag   2160
agatgagaga ccactctttc cccaaattct cgcctctatt gagctgctgg cccgctcatt   2220
gccaaaaatt caccgcagtg catcagaacc ctccttgaat cggggctggtt tccaaacaga   2280
ggattttagt ctatatgctt gtgcttctcc aaaaacaccc atccaggcag gggatatgg    2340
tgcgtttcct gtccactgaa acaaatgagt gagagagttc aggagagtag caacaaaagg   2400
```

-continued aaaataaatg aacatatgtt tgcttatatg ttaaattgaa taaaatactc tcttttttt 2460 taaggtggaa aaaaaaaaa aaaaaaaaaa aaaaaaaaaa aaaaaaaccc 2510

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
attttgaagg agacggactg 20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
tggattttga aggagacgga 20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
cgttagttag tgagccaggt 20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
atttctgtaa ggctttcacg 20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
cccgtctacc aagtgttttc 20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
aatctcccaa tcatcactcg 20

<210> SEQ ID NO 74
<211> LENGTH: 20

```
<212> TYPE: DNA
<213> ORGANISM: Artificial Sequence
<220> FEATURE:
<223> OTHER INFORMATION: Synthetic

<400> SEQUENCE: 74

tgctgaggtg taggtgctgt                                              20


<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75

tgtaactgct gaggtgtagg                                              20


<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76

tgtcgtgttt tcctgagtac                                              20


<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77

agttgtggct ttgtggaata                                              20


<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78

atggagatgg tgatacaagc                                              20


<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79

ggatgattga cttggcgtgt                                              20


<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
```

aggtctctgt ggatgattga 20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
attctgatga cttctggtgc 20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
gctgtatgga tttttatctt 20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
tacagaacaa tcccaaatgc 20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
atcctcgtcc caccataaaa 20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
ctctcatctc ttttcttttt 20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
gtctctcatc tcttttcttt 20

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
ccgattcaag gagggttctg 20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
tggatgggtg tttttggaga 20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
ctgcctggat gggtgttttt 20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
ggacaggaaa cgcaccatat 20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
ctcatttgtt tcagtggaca 20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
tctctcactc atttgtttca 20

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
actctctcac tcatttgttt 20

-continued

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
gaactctctc actcatttgt 20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
tcctgaactc tctcactcat 20

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
ttgctactct cctgaactct 20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
tttgttgcta ctctcctgag 20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
cttttgttgc tactctcctg 20

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
gctactctcc tgaactctct 20

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
ttccttttgt tgctactctc 20

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
atttattttc cttttgttgc 20

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
atatgttcat ttattttcct 20

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
tttattttcc ttttgttgct 20

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
tgttcattta ttttcctttt 20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
atttaacata taagcaaaca 20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
ctgcctggta ccctgttttt 20

<210> SEQ ID NO 107

-continued

```
<211> LENGTH: 20
<212> TYPE: DNA
<213> ORGANISM: Artificial Sequence
<220> FEATURE:
<223> OTHER INFORMATION: Synthetic

<400> SEQUENCE: 107

ctgcctggaa gggtgttttt                                        20


<210> SEQ ID NO 108
<211> LENGTH: 20
<212> TYPE: DNA
<213> ORGANISM: Artificial sequence
<220> FEATURE:
<223> OTHER INFORMATION: Synthetic

<400> SEQUENCE: 108

ctgcctggta cggtgttttt                                        20
```